United States Patent [19]

Maddox

[11] 4,289,406

[45] Sep. 15, 1981

[54] LIGHT TRANSMISSION MEASUREMENT METHOD

[75] Inventor: William J. Maddox, Lancaster, Pa.

[73] Assignee: RCA Corporation, New York, N.Y.

[21] Appl. No.: 18,909

[22] Filed: Mar. 9, 1979

[51] Int. Cl.³ .................... G01N 21/84; G01N 21/86
[52] U.S. Cl. .................................. 356/429; 250/571; 356/434
[58] Field of Search ...................... 356/429, 434, 430; 250/559, 571, 572

[56] References Cited

U.S. PATENT DOCUMENTS

| 3,690,772 | 9/1972 | Endl | 356/434 X |
| 3,790,289 | 2/1974 | Schmidt | 356/434 |
| 3,808,067 | 4/1974 | Brown | 156/626 |
| 4,099,607 | 7/1978 | Brennan et al. | 198/341 |
| 4,126,510 | 11/1978 | Moscony et al. | 156/626 |

Primary Examiner—Vincent P. McGraw
Assistant Examiner—Rodney B. Bovernick
Attorney, Agent, or Firm—Eugene M. Whitacre; Glenn H. Bruestle; Vincent J. Coughlin, Jr.

[57] ABSTRACT

A method is provided for measuring light transmission through a continuous sheet having an aperture pattern thereon. A light source is positioned on one side of the sheet and a light sensor is positioned on the opposite side of the sheet. The improvement comprises bypassing a portion of the light from the light source around the sheet to the sensor. The bypassed light is used to update the calibration of the measurements.

2 Claims, 1 Drawing Figure

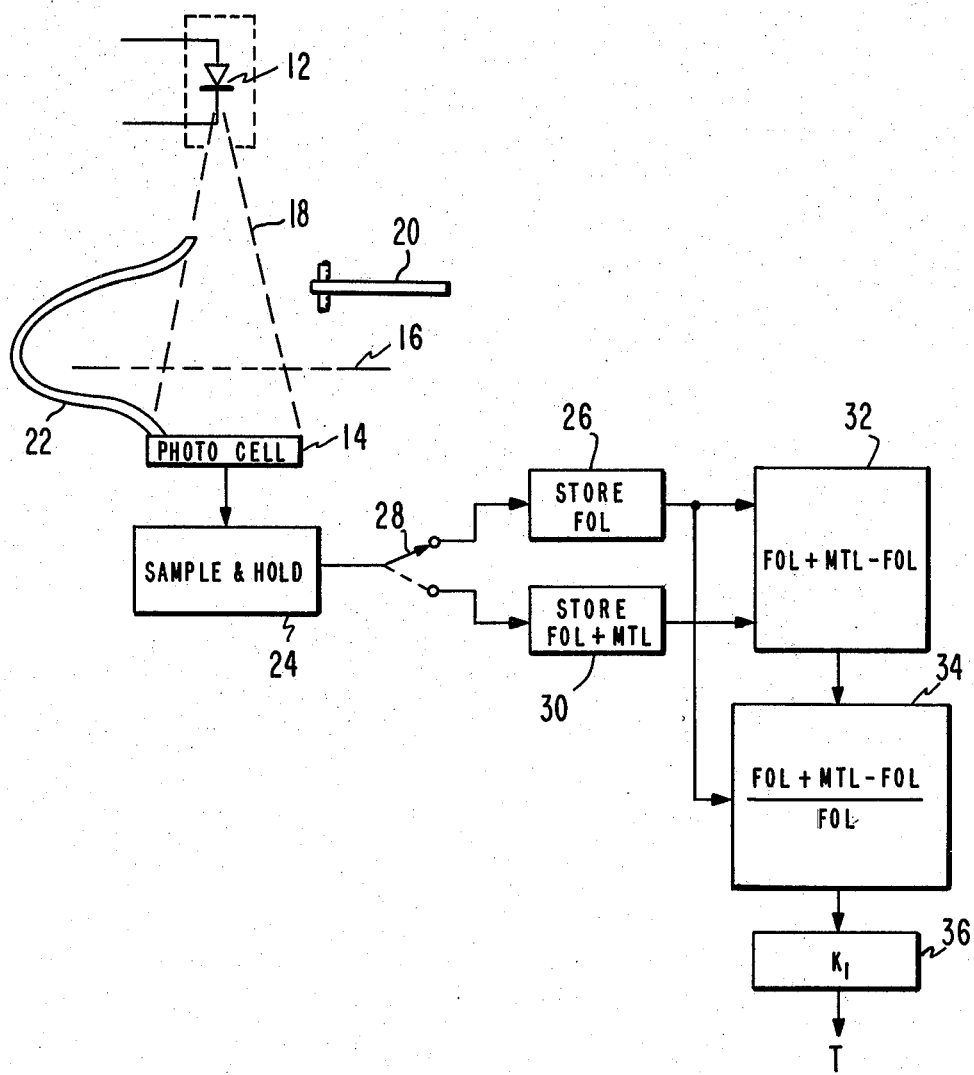

LIGHT TRANSMISSION MEASUREMENT METHOD

This invention relates to methods and apparatus for measuring light transmission of a continuous sheet having a series of apertured patterns thereon.

In the manufacture of apertured masks, such as used in color television picture tubes, a roll of sheet metal first is coated with a photoresist material and then is photoexposed to form a series of mask patterns. Subsequently, the sheet metal roll is processed through an etchant bath to open apertures forming each mask pattern. After etching has been completed, the apertured mask patterns are checked to determine if a desired level of light transmission has been achieved. Although there have been many ways suggested by the prior art for performing this transmission check, the principal method in use utilizes a light source on one side of an apertured pattern and a light sensor on the other side. When the transmission check is made on the etch line before the individual masks are removed from the metal sheet, it is necessary that all components of the measuring system remain constant if accurate transmissions are to be determined. Unfortunately, various factors affect the system components so that accuracies of transmission measurements will change over a period of time. These factors include variations in the light source, the light sensor and the electronics which occur with age and with environmental changes. Therefore, it is desirable to develop a light transmission measuring method that can automatically account for the aforementioned variations.

SUMMARY OF THE INVENTION

A method is provided for measuring light transmission through a continuous sheet having an aperture pattern thereon. A light source is positioned on one side of the sheet and a light sensor is positioned on the opposite side of the sheet. The improvement comprises bypassing a portion of the light from the light source around the sheet to the sensor. The bypassed light is used to update the calibration of the measurements.

BRIEF DESCRIPTION OF THE DRAWING

The single drawing is a schematic diagram of a light transmission measurement system showing the functions of various electronic components in block diagram form.

DETAILED DESCRIPTION

One embodiment of a light transmission measuring system 10 for practicing the present novel method is shown in the drawing. The system 10 includes a light source 12, such as the light emitting diode shown, and a facing light sensor 14, such as a photo cell. Located between the light source 12 and the sensor 14, is a continuous metal sheet 16 having a series of separated aperture patterns thereon. The drawing illustrates the boundary of light rays 18 emitted from the light source 12 passing through one aperture pattern on the sheet 16. Slightly below the light source 12, a shutter 20 is shown in its retracted position. The shutter 20 is used during calibration of the system 10. Also shown, is a fiber optics light pipe 22 having one end inside the boundary of the light rays 18 and the other end pointed at an active portion of the light sensor 14. The light pipe 22 bypasses a portion of the light emitted from the light source 12 around the sheet 16 to the sensor 14. The remaining portion of the system 10 will be described with respect to the novel method.

The system 10 initially is calibrated without the sheet 16 in place. First, the shutter 20 is rotated to block all of the light rays from the light source except those rays entering the fiber optic light pipe 22. The output of the light sensor 14 is now recorded. Next, the shutter is retracted so that the light sensor 14 is fully exposed by the light source 12 with sheet 16 still absent. Now, the sensor output from this step is divided into the sensor output when light passed only through the light pipe 22 to obtain a ratio relating exposure only through the light pipe 22 to total sensor exposure. This ratio will be used in the final step in calculating light transmission.

Once the system 10 is calibrated, the sheet 16 can be inserted between the light source 12 and sensor 14. When no aperture pattern is present between the light source 12 and sensor 14, such as between aperture patterns, the sheet 16 will cut off all light transmission between the light source 12 and the sensor 14 except that portion of the light passing through the light pipe 22. The sensor output for this condition, designated FOL, is fed into a sample and hold unit 24 and then fed into a storage unit 26 through a two way switch 28. If all the components of the system 10 were constant, this output FOL would equal the output obtained for the light pipe transmission during the calibration procedure.

As the sheet 16 moves, an aperture pattern is positioned between the light source 12 and the sensor 14. Some percentage of the light rays 18 will now pass through the apertures of the pattern. The sensor output, designated FOL+MTL, now is a function of both the light bypassed by the lightpipe 22 and the light transmitted through the aperture pattern. This output again goes through the sample and hold unit 24 but this time is directed to a second storage unit 30 by movement of the switch 28 to its alternate position shown by the dashed line in the drawing. At this point, sufficient information is ready for determination of the aperture pattern light transmission.

The two outputs, FOL and FOL+MTL, stored in the units 26 and 30 respectively, are fed to a subtracting unit 32 which subtracts the FOL output from the FOL+MTL output to obtain a signal solely indicative of pattern transmission. Next, this signal is divided by the output FOL in another unit 34. The division step normalizes the transmission value associated with the pattern which in effect removes inaccuracies caused by variations in system components. Thereafter, the output from unit 34 is fed to another unit 36 where it is multiplied by the initially calculated constant K, to obtain the light transmission T of the pattern under test.

The following example shows how the present method will produce constant results even though the system calibration changes by 40% over the length of a roll of metal sheet material. In the example, all aperture patterns have an actual transmission of 25%.

EXAMPLE

| Initial Calibration | Sensor Output |
|---|---|
| Light pipe only with remainder shuttered | 1 unit |
| Light pipe with remainder unshuttered | 20 units |
| Constant | |

-continued $$K_1 = \frac{1}{20}$$

Test Data
Early Sheet Pattern

| | |
|---|---|
| Light pipe only with sheet between patterns (FOL) | 1 unit |
| Transmission through pattern (MTL) | 5 units |

Middle Sheet Pattern

| | |
|---|---|
| Light pipe only with sheet between patterns (FOL) | .8 unit |
| Transmission through pattern (MTL) | 4 units |

Later Sheet Pattern

| | |
|---|---|
| Light pipe only with sheet between patterns (FOL) | .6 unit |
| Transmission through pattern (MTL) | 3 units |

Transmission Calculations
Early Sheet Pattern $$T = K_1 \frac{FOL + MTL - FOL}{FOL} = \frac{1}{20} \times \frac{1 + 5 - 1}{1} = .25 = 25\%$$

Middle Sheet Pattern $$T = K_1 \frac{FOL + MTL - FOL}{FOL} = \frac{1}{20} \times \frac{.8 + 4 - .8}{.8} = .25 = 25\%$$

Later Sheet Pattern $$T = K \frac{FOL + MTL - FOL}{FOL} = \frac{1}{20} \times \frac{.6 + 3 - .6}{.6} = .25 = 25\%$$

Therefore, from the above example, it can be seen that regardless of drift in the system components, the method will always produce the correct transmission value.

Specific electronic components for practicing the present method as described herein are well known in the art and will not be described further. In addition, it also should be recognized that the calculations required for the method easily could be performed manually.

I claim:

1. In a method for measuring light transmission through a continuous sheet having a series of separated aperture patterns thereon wherein a light source is positioned on one side of the sheet and a light sensor is positioned on the opposite side of the sheet, the improvement comprising continuously bypassing a portion of the light from said light source around said sheet to said light sensor, recording the sensor output when direct light to said sensor is obstructed, recording the sensor output when direct light to said sensor is unobstructed, and dividing the obstructed sensor output by the unobstructed sensor output to obtain a system ratio, first measuring sensor output when direct light is blocked from said sensor, second measuring sensor output when an aperture pattern is located between said light source and said sensor, subtracting the first measured sensor output from the second measured sensor output to obtain an output difference, dividing the output difference by the first measured sensor output to obtain a normalized value, and multiplying the normalized value by said system ratio to obtain the transmission ratio of a particular aperture pattern.

2. The method as defined in claim 1 wherein the bypassed portion of light is bypassed through a fiber optics light pipe which extends around an edge of the sheet.

* * * * *